United States Patent
Watanabe et al.

(10) Patent No.: US 10,175,220 B2
(45) Date of Patent: Jan. 8, 2019

(54) IMAGE PROCESSING DEVICE, PATHOLOGICAL DIAGNOSIS SUPPORT SYSTEM, STORAGE MEDIUM FOR IMAGE PROCESSING, AND IMAGE PROCESSING METHOD

(71) Applicant: Konica Minolta, Inc., Tokyo (JP)

(72) Inventors: Yasuhiro Watanabe, Hachioji (JP); Shuji Ichitani, Hachioji (JP); Kohsuke Gonda, Sendai (JP); Noriaki Ohuchi, Sendai (JP); Mika Watanabe, Sendai (JP)

(73) Assignee: KONICA MINOLTA, INC., Tokyo (JP)

( * ) Notice: Subject to any disclaimer, the term of this patent is extended or adjusted under 35 U.S.C. 154(b) by 257 days.

(21) Appl. No.: 15/103,171

(22) PCT Filed: Dec. 17, 2014

(86) PCT No.: PCT/JP2014/083379
§ 371 (c)(1),
(2) Date: Jun. 9, 2016

(87) PCT Pub. No.: WO2015/093518
PCT Pub. Date: Jun. 25, 2015

(65) Prior Publication Data
US 2018/0164277 A1    Jun. 14, 2018

(30) Foreign Application Priority Data

Dec. 18, 2013 (JP) ................. 2013-260769

(51) Int. Cl.
*G06K 9/00* (2006.01)
*G01N 33/483* (2006.01)
(Continued)

(52) U.S. Cl.
CPC ....... *G01N 33/4833* (2013.01); *A61B 5/0071* (2013.01); *G06K 9/0014* (2013.01);
(Continued)

(58) Field of Classification Search
USPC ....... 382/100, 103, 106, 128–133, 162, 168, 382/181, 189, 203, 209, 219, 224, 232,
(Continued)

(56) References Cited

U.S. PATENT DOCUMENTS

| 5,097,135 A | 3/1992 | Makino et al. |
| 2008/0052009 A1 | 2/2008 | Chiu et al. |

(Continued)

FOREIGN PATENT DOCUMENTS

| JP | S6366465 A | 3/1988 |
| WO | 2012029342 A1 | 3/2012 |
| WO | 2013/146841 A1 | 10/2013 |

OTHER PUBLICATIONS

International Search Report dated Mar. 24, 2015 for PCT/JP2014/083379 and English translation.
(Continued)

*Primary Examiner* — Seyed Azarian
(74) *Attorney, Agent, or Firm* — Lucas & Mercanti, LLP

(57) ABSTRACT

An image processing device (2A) comprises: an input means for inputting a brightfield image representing cell morphology in a tissue section, and a fluorescence image representing, by fluorescent bright spots, the expression of a specific protein in the same range of the tissue section; a first generation means for generating a cell image obtained by extracting a specific site of a cell from the brightfield image; a second generation means for generating an image obtained by extracting bright spot regions from the fluorescence image, creating a brightness profile for each bright spot region, and generating a fluorescent particle image obtained
(Continued)

by extracting the fluorescent particles in the bright spot regions on the basis of the fluorescence profile for one fluorescent particle, which serves as a fluorescence bright spot source; and a calculation means for superimposing the cell image and the fluorescent particle image on one another.

6 Claims, 18 Drawing Sheets

(51) Int. Cl.
    *G06T 5/50*     (2006.01)
    *G06T 7/11*     (2017.01)
    *A61B 5/00*     (2006.01)
    *G06T 7/00*     (2017.01)
    *H04N 7/18*     (2006.01)

(52) U.S. Cl.
    CPC .............. *G06T 5/50* (2013.01); *G06T 7/0012* (2013.01); *G06T 7/11* (2017.01); *G06T 2207/10064* (2013.01); *G06T 2207/20221* (2013.01); *G06T 2207/30024* (2013.01)

(58) Field of Classification Search
    USPC ....... 382/254, 274, 276, 285–291, 312, 321; 359/383; 348/79, 222.1; 506/8
    See application file for complete search history.

(56) References Cited

U.S. PATENT DOCUMENTS

| | | | |
|---|---|---|---|
| 2009/0086314 A1* | 4/2009 | Namba | G01N 21/6458 359/383 |
| 2011/0249137 A1* | 10/2011 | Suzuki | G01N 21/6428 348/222.1 |
| 2013/0338016 A1* | 12/2013 | McDonough | G06F 19/18 506/8 |
| 2014/0267672 A1* | 9/2014 | Morrison | G01N 21/6458 348/79 |
| 2014/0314299 A1* | 10/2014 | Santamaria-Pang | G06K 9/0014 382/133 |
| 2015/0049936 A1 | 2/2015 | Tsunomori et al. | |

OTHER PUBLICATIONS

Office Action dated Jun. 22, 2018 from corresponding European Application No. 14870827.4.

IPRP dated Mar. 24, 2015; International Application No. PCT/JP2014/083379; Applicant: Konica Minolta, Inc.; English translation of IPRP; Total of 8 pages.

Extended European Search Report dated May 18, 2017 from corresponding European Application No. 14870827.4; Applicant: Konica Minolta, Inc.; Total of 8 pages.

* cited by examiner

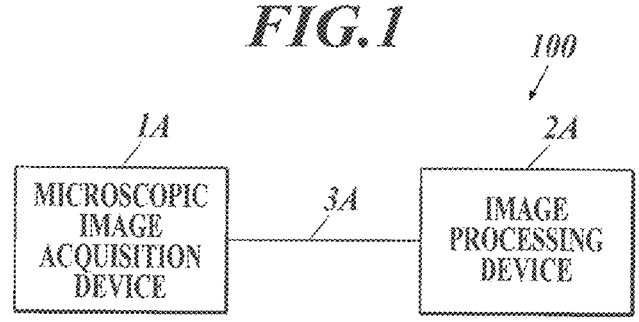
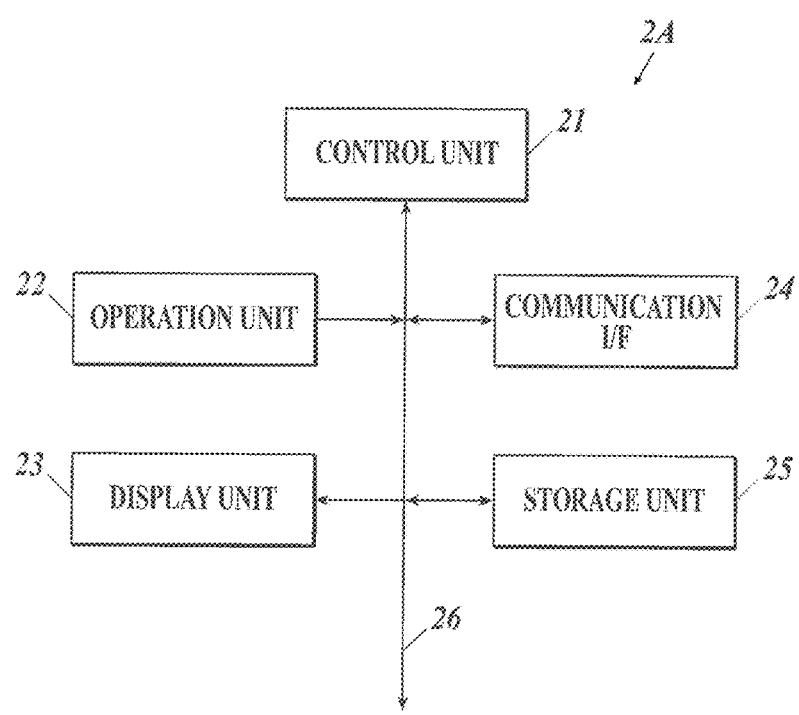

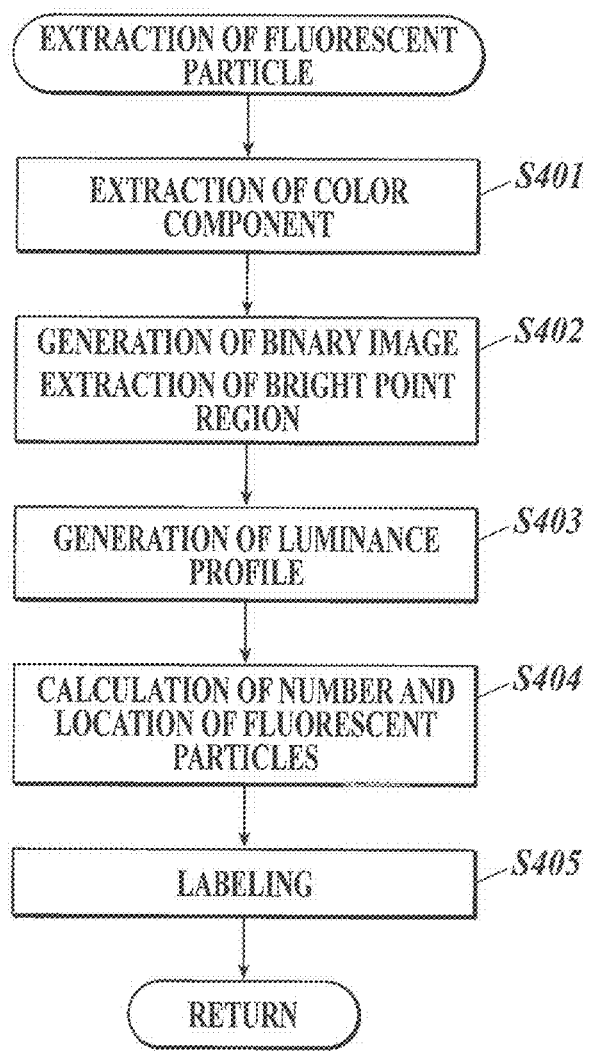

| | | | | | | | COORDINATE X | | | | | | | | | | |
|---|---|---|---|---|---|---|---|---|---|---|---|---|---|---|---|---|---|
| | 37 | 26 | 64 | | | | | | | | 62 | 63 | 13 | | | | |
| | 59 | 31 | 59 | 69 | | | | | | 41 | 56 | 43 | 40 | 65 | | | |
| | 34 | 69 | 59 | 34 | 45 | 22 | 50 | 77 | 57 | 68 | 55 | 68 | 69 | 42 | 51 | 63 | |
| | | 42 | 59 | 33 | 38 | 37 | 66 | 78 | 53 | 90 | 89 | 92 | 83 | 43 | 74 | 75 | |
| | | 29 | 8 | 24 | 46 | 22 | 54 | 65 | 40 | 105 | 81 | 120 | 75 | 72 | 77 | 58 | |
| | | 35 | 13 | 27 | 52 | 6 | 26 | 95 | 129 | 124 | 88 | 108 | 123 | 101 | 64 | 84 | |
| | | 45 | 4 | 38 | 19 | 31 | 131 | 212 | 311 | 290 | 182 | 79 | 76 | 86 | 82 | 62 | |
| | | 37 | 29 | 15 | 10 | 58 | 278 | 538 | 680 | 518 | 319 | 116 | 80 | 88 | 82 | 62 | |
| 53 | 55 | 31 | 26 | 33 | 69 | 124 | 374 | 701 | 823 | 782 | 398 | 155 | 84 | 92 | 88 | 42 | |
| 42 | 62 | 25 | 53 | 51 | 36 | 135 | 393 | 577 | 740 | 561 | 335 | 131 | 112 | 97 | 72 | 48 | 89 |
| 44 | 41 | 23 | 45 | 42 | 76 | 115 | 256 | 390 | 481 | 341 | 160 | 101 | 72 | 86 | 66 | 75 | 91 |
| | | 28 | 36 | 55 | 87 | 120 | 159 | 156 | 211 | 135 | 147 | 90 | 64 | 69 | | | |
| | | 22 | 64 | 58 | 62 | 82 | 103 | 122 | 137 | 111 | 109 | 105 | 108 | 91 | | | |
| | | 77 | 73 | 49 | 55 | 81 | 101 | 96 | 117 | 114 | 109 | | | | | | |
| | | 42 | 39 | 52 | 49 | 45 | 80 | 90 | 69 | 98 | 104 | | | | | | |
| | | 26 | 47 | 35 | 35 | 88 | | | | | | | | | | | |

IMAGE PROCESSING DEVICE, PATHOLOGICAL DIAGNOSIS SUPPORT SYSTEM, STORAGE MEDIUM FOR IMAGE PROCESSING, AND IMAGE PROCESSING METHOD

CROSS REFERENCE TO RELATED APPLICATION

This Application is a 371 of PCT/JP2014/083379 filed on Dec. 17, 2014, which, in turn, claimed the priority of Japanese Patent Application No. JP2013-260769 filed on Dec. 18, 2013, both applications are incorporated herein by reference.

TECHNICAL FIELD

The present invention relates to an image processing device, a pathological diagnosis support system, an image processing program and an image processing method.

BACKGROUND ART

In recent years, with the spread of therapy using molecular target drugs based mainly on antibody drugs, quantitating biological substances (antigens) in cells of the observation target has been desired for more efficient design of the molecular target drugs. For confirming the presence of a biological substance, a method of organization analysis is known on the basis of the binding of a fluorescent substance bonded with biological substance recognition site and a biological substance which bind the biological substance recognition site.

Patent Document 1 suggests a method for identifying specific cells and quantification, including staining a tissue slice with a fluorescent dye and calculating the area and the luminance level of light emitting parts (see line 13 in lower right column on page 3 to line 8 in upper left column on page 4; lines 10 to 14 in lower left column on page 4, etc.).

Unfortunately, according the method, the number and the location of biological substances in cells cannot be obtained accurately on the basis of luminance level, because emitted lights superimpose with each other when there are many biological substances in a specific small area in one cell.

In contrast, Patent Document 2 describes a method for calculating the number of bright points per cell, including staining a tissue slice with a fluorescent particle and measuring fluorescent bright points using a confocal microscope (see Examples 1-2).

CITATION LIST

Patent Literature

Patent Literature 1: Japanese Patent Laid-open Publication No. 63-066465
Patent Literature 2: International Publication No. 2012/029342

SUMMARY OF INVENTION

Problems to be Solved by Invention

According to the method, the number of biological substances in observation target cells can be quantitated. However, the information regarding the location of the biological substances in cells cannot be obtained and use of a confocal microscope causes a problem of taking labor and reduced simplicity.

Accordingly, the main objects of the present invention are to provide an image processing device which can easily and accurately quantitate expression of a specific protein (the amount and the location of expressed protein) in observation target cells and also to provide a pathological diagnosis support system utilizing the image processing device, an image processing program, and an image processing method.

Means for Solving Problems

In order to solve the above problems, according to a first aspect of the present invention, there is provided an image processing device including:

an input unit to input a bright field image showing a shape of a cell in a tissue section and a fluorescence image showing expression of a specific protein as a fluorescent bright point in the same range of the tissue section as the bright field image;

a first generation unit to generate a cell image showing an extracted specific site of the cell from the bright field image;

a second generation unit to generate an image showing an extracted bright point region from the fluorescence image, to generate a luminance profile for the bright point region, and to generate a fluorescent particle image showing an extracted fluorescent particle in the bright point region on the basis of a luminance profile of one fluorescent particle which is a source of fluorescent bright point; and an addition unit to add the cell image and the fluorescent particle image.

According to a second aspect of the present invention, there is provided a pathological diagnosis support system including:

the image processing device; and an image acquisition device to acquire the bright field image and the fluorescence image used in the image processing device.

According to a third aspect of the present invention, there is provided an image processing program to cause a computer to function as:

an input unit to input a bright field image showing a shape of a cell in a tissue section and a fluorescence image showing expression of a specific protein as a fluorescent bright point in the same range of the tissue section as the bright field image;

a first generation unit to generate a cell image showing an extracted specific site of the cell from the bright field image;

a second generation unit to generate an image showing an extracted bright point region from the fluorescence image, to generate a luminance profile for the bright point region, and to generate a fluorescent particle image showing an extracted fluorescent particle in the bright point region on the basis of a luminance profile of one fluorescent particle which is a source of fluorescent bright point; and an addition unit to add the cell image and the fluorescent particle image.

According to a fourth aspect of the present invention, there is provided an image processing method including;

an input step of inputting a bright field image showing a shape of a cell in a tissue section and a fluorescence image showing expression of a specific protein as a fluorescent bright point in the same range of the tissue section as the bright field image;

a first generation step of generating a cell image showing an extracted specific site of the cell from the bright field image;

a second generation step of generating an image showing an extracted bright point region from the fluorescence image, to generate a luminance profile for the bright point region, and to generate a fluorescent particle image showing an extracted fluorescent particle in the bright point region on the basis of a luminance profile of one fluorescent particle which is a source of fluorescent bright point; and an addition step of adding the cell image and the fluorescent particle image.

Effects of Invention

According to the present invention, it is possible to easily and accurately quantitate expression of a specific protein (the amount and the location of expressed protein) in observation target cells.

BRIEF DESCRIPTION OF THE DRAWINGS

FIG. 1 shows the system configuration of a pathological diagnosis support system.

FIG. 2 is a block diagram showing the functional configuration of an image processing device shown in FIG. 1.

FIG. 8 is a flowchart showing details of processing of Step S4 in FIG. 5.

MODES FOR CARRYING OUT THE INVENTION

Figure 3:
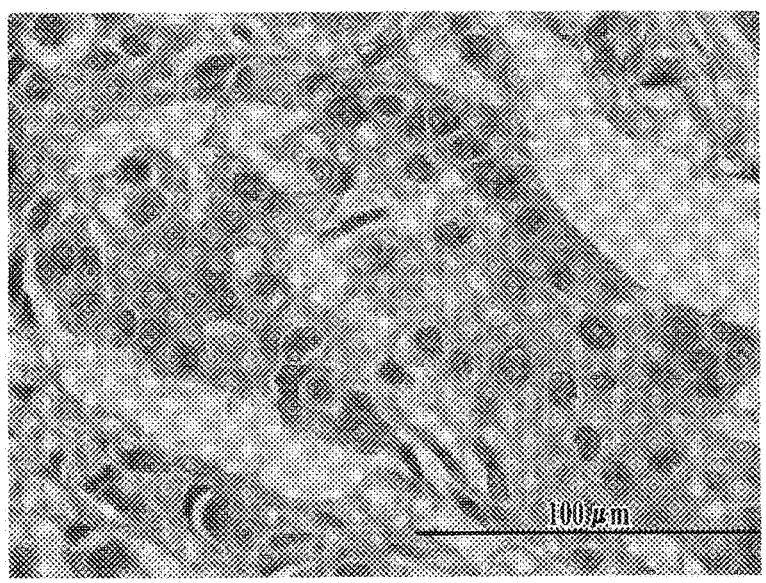
FIG. 3 shows an example of a bright field image.

Embodiments of the present invention are described below by referring to the drawings. However, the present invention is not limited thereto.

<Configuration of Pathological Diagnosis Support System 100>

FIG. 1 shows an example of the overall configuration of a pathological diagnosis support system 100 of an embodiment. The pathological diagnosis support system 100 acquires a microscopic image of a tissue section of a human body stained with a predetermined staining reagent and analyzes the acquired microscopic image so as to output a feature amount quantitatively showing expression of a specific biological substance in the tissue section as an observation target.

As shown in FIG. 1, the pathological diagnosis support system 100 includes a microscopic image acquisition device 1A and an image processing device 2A which are connected to each other through an interface such as a cable 3A so as to send and receive data therebetween. The method of connecting the microscopic image acquisition device 1A and the image processing device 2A is not particularly limited. For example, the microscopic image acquisition device 1A and the image processing device 2A may be connected by a LAN (Local Area Network) or be connected wirelessly.

The microscopic image acquisition device 1A is a well-known camera-attached optical microscope. The microscopic image acquisition device 1A acquires a microscopic image of a tissue section on a slide placed on a slide fixing stage and sends the image to the image processing device 2A.

The microscopic image acquisition device 1A includes an irradiating unit, an image forming unit, an imaging unit, and a communication I/F. The irradiating unit includes a light source and a filter and irradiates, with light, the tissue section on the slide placed on the slide fixing stage. The image forming unit includes an ocular lens and an object lens and forms an image of transmitted light, reflected light, or fluorescence emitted from the tissue section on the slide owing to the light with which the tissue section has been irradiated. The imaging unit is the camera set in the microscope and includes a CCD (Charge Coupled Device) sensor and captures the image formed on an image forming face by the image forming unit so as to generate digital image data of a microscopic image. The communication I/F sends the generated image data of the microscopic image to the image processing device 2A. In the embodiment, the microscopic image acquisition device 1A includes: a bright field unit in which an irradiating unit and an image forming unit suitable for bright field observation are combined; and a fluorescence unit in which an irradiating unit and an image forming unit suitable for fluorescence observation are combined, and can switch the bright field and the fluorescence by switching the bright field unit and the fluorescence unit.

The microscopic image acquisition device 1A is not limited to a camera-attached microscope. For example, an apparatus for creating a virtual microscope slide, the apparatus scanning a slide on a slide fixing stage of a microscope so as to acquire a microscopic image of the entire tissue section, can be used. (Refer to, for example, Japanese Patent Application Publication No. 2002-514319). The apparatus for creating a virtual microscope slide can acquire image data with which an image of the entire tissue section on the slide can be viewed at once on a display unit.

The image processing device 2A analyzes the microscopic image sent from the microscopic image acquisition device 1A so as to calculate the expression distribution of a specific biological substance in a tissue section as an observation target.

FIG. 2 shows an example of the functional configuration of the image processing device 2A. As shown in FIG. 2, the image processing device 2A includes a control unit 21, an operation unit 22, a display unit 23, a communication I/F 24, and a storage unit 25, and these units and the like are connected to each other through a bus 26.

The control unit 21 includes a CPU (Central Processing Unit) and a RAM (Random Access Memory). The control unit 21 performs a various types of processing by working together with various programs stored in the storage unit 25 and collectively controls operation of the image processing device 2A. For example, the control unit 21 performs an image analysis process (shown in FIG. 5) by working together with a program(s) stored in the storage unit 25 and functions as a first generation unit, a second generation unit, and an addition unit.

The operation unit 22 includes: a keyboard provided with character input keys, number input keys and various function keys; and a pointing device such as a mouse, and outputs press signals of the keys pressed on the keyboard and operation signals of the mouse to the control unit 21 as input signals.

The display unit 23 includes a monitor such as a CRT (Cathode Ray Tube) or an LCD (Liquid Crystal Display), and displays thereon various screens in response to instructions of display signals input from the control unit 21. In the embodiment, the display unit 23 functions as an output unit to output the result of image analysis.

The communication I/F 24 is an interface to send/receive data to/from external devices such as the microscopic image acquisition device 1A. The communication I/F 24 functions as an input unit to input bright field images and fluorescence images.

The storage unit 25 includes an HDD (Hard Disk Drive) and a nonvolatile semiconductor memory. The storage unit 25 stores therein the above-described various programs, various data and so forth.

The image processing device 2A may include a LAN adapter, a router and so forth and be connected to external devices through a communication network such as a LAN.

The image processing device 2A of the embodiment preferably analyzes bright field images (H-stained images or HE-stained images) and fluorescence images sent from the microscopic image acquisition device 1A.

The bright field image is a microscopic image acquired by, in the microscopic image acquisition device 1A, forming and capturing an enlarged image of a tissue section stained with an H (hematoxylin) staining reagent or an HE (hematoxylin-eosin) staining reagent with a bright field. The bright field image is a cell shape image showing shapes of cells in the tissue section. Hematoxylin is a blue-violet dye and stains cell nuclei, bony tissue, a part of cartilaginous tissue, serous components and so forth (basophilic tissue or the like). Eosin is a red to pink dye and stains cytoplasm, connective tissue of soft tissue, red blood cells, fibrin, endocrine granules and so forth (acidophilic tissue or the like). FIG. 3 shows an example of a bright field image acquired by capturing an HE-stained tissue section.

Figure 4:
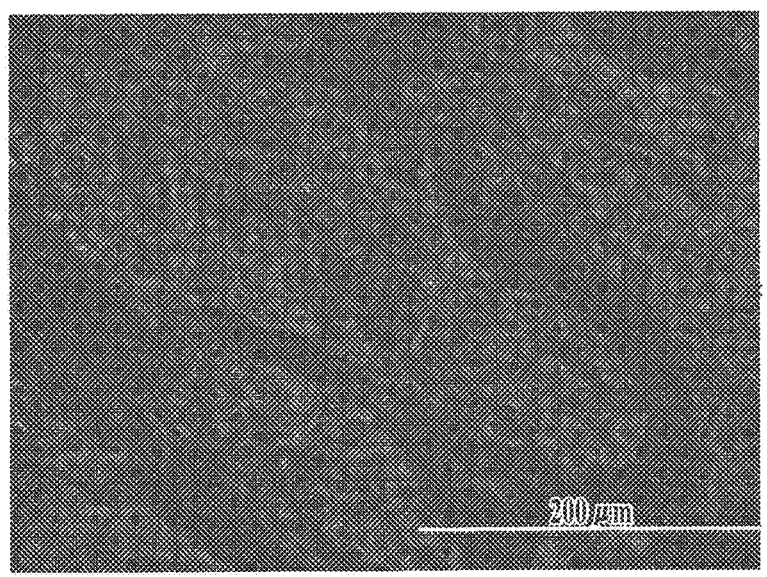
FIG. 4 shows an example of a fluorescence image.

The fluorescence image is a microscopic image acquired by, in the microscopic image acquisition device 1A, irradiating, with excitation light having a predetermined wavelength, a tissue section stained with a staining reagent including nanoparticles containing a fluorescent substance (hereinafter called "fluorescent substance-containing nanoparticles") bonded with a biological substance recognition site which specifically bonds and/or reacts with a specific biological substance so as to make the fluorescent substance-containing nanoparticles emit light (fluorescence), and forming and capturing an enlarged image of the fluorescence. In other words, the fluorescence appearing in a fluorescence image shows expression of a specific biological substance, which corresponds to a biological substance recognition site, in a tissue section. FIG. 4 shows an example of a fluorescence image.

<Acquisition of Fluorescence Image>

Here, the method of acquiring fluorescence images is described in detail as well as the staining reagent (the fluorescent substance-containing nanoparticles) used to acquire fluorescence images and the method of staining tissue sections with the staining reagent.

[Fluorescent Substance]

Examples of the fluorescent substance used in the staining reagent to acquire fluorescence images include a fluorescent organic dye and a quantum dot (semiconductor particles). Preferably, the substance exhibits emission of visible to near infrared rays having a wavelength within the range from 400 to 1100 nm when excited by ultraviolet to near infrared rays having a wavelength within the range from 200 to 700 nm.

Examples of the fluorescent organic dye include fluorescein dye molecules, rhodamine dye molecules, Alexa Fluor (manufactured by Invitrogen Corporation) dye molecules, BODIPY (manufactured by Invitrogen Corporation) dye molecules, cascade dye molecules, coumarin dye molecules, eosin dye molecules, NBD dye molecules, pyrene dye molecules, Texas Red dye molecules and cyanine dye molecules.

Specific examples thereof include 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 6G, tetramethylrhodamine, X-rhodamine, and Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (the above are manufactured by Invitrogen Corporation), methoxycoumalin, eosin, NBD, pyrene, Cy5, Cy5.5 and Cy7. These can be used individually, or multiple types thereof may be mixed to use.

Usable examples of the quantum dot include quantum dots respectively containing, as a component, II-VI compounds, III-V compounds and IV elements (called "II-VI quantum dot", "III-V quantum dot" and "IV quantum dot", respectively). These can be used individually, or multiple types thereof may be mixed to use.

Specific examples thereof include but are not limited to CdSe, CdS, CdTe, ZnSe, ZnS, ZnTe, InP, InN, InAs, InGaP, GaP, GaAs, Si and Ge.

A quantum dot having a core of any of the above quantum dots and a shell provided thereon can also be used. Hereinafter, in this specification, as a notation for the quantum dot having a shell, when the core is CdSe and the shell is ZnS, the quantum dot is noted as CdSe/ZnS. Usable examples of the quantum dot include but are not limited to CdSe/ZnS, CdS/ZnS, InP/ZnS, InGaP/ZnS, Si/SiO$_2$, Si/ZnS, Ge/GeO$_2$ and Ge/ZnS.

A quantum dot having a surface treated with an organic polymer or the like may be used as needed. Examples thereof include CdSe/ZnS having a surface carboxy group (manufactured by Invitrogen Corporation) and CdSe/ZnS having a surface amino group.

[Fluorescent Substance-Containing Nanoparticles]

The fluorescent substance-containing nanoparticles of the embodiment are nanoparticles in which a fluorescent substance is dispersed. The fluorescent substance and the nanoparticles may or may not chemically bond with each other.

The material for the nanoparticles is not particularly limited, and examples thereof include polystyrene, polyactate, silica, and melamine.

The fluorescent substance-containing nanoparticles used in the embodiment can be produced by a well-known method. For example, fluorescent organic dye-containing silica nanoparticles can be synthesized by referring to synthesis of FITC-containing silica nanoparticles described in Langmuir, vol. 8, page 2921 (1992). A variety of fluorescent organic dye-containing silica nanoparticles can be synthesized by using any desired fluorescent organic dye instead of FITC.

Quantum dot-containing silica nanoparticles can be synthesized by referring to synthesis of CdTe-containing silica nanoparticles described in New Journal of Chemistry, vol. 33, page 561 (2009).

Fluorescent organic dye-containing polystyrene nanoparticles can be produced by using a copolymerization method using an organic dye having a polymerizable functional group described in U.S. Pat. No. 4,326,008 (1982) or a method of impregnating a fluorescent organic dye into polystyrene nanoparticles described in U.S. Pat. No. 5,326,692 (1992).

Quantum dot-containing polymer nanoparticles can be produced by using a method of impregnating a quantum dot into polystyrene nanoparticles described in Nature Biotechnology, vol. 19, page 631 (2001).

The average particle size of the fluorescent substance-containing nanoparticles used in the embodiment is not particularly limited, and the nanoparticles having an average particle size of about 30 to 800 nm can be used. Further, the variation coefficient (=(standard deviation/average value)×100%) showing dispersion of particle sizes is not particularly limited, and the nanoparticles having a variation coefficient of 20% or less is preferable to use. The average particle size is obtained as follows: take an electronic microscopic picture using a scanning electron microscope (SEM) so as to measure cross-sectional areas of a sufficient number of particles; and, taking the measured values as the areas of circles, obtain diameters of the circles as particle sizes. In the present application, the average particle size is an arithmetical mean of particle sizes of 1,000 particles, and the variation coefficient is a value calculated from distribution of particle sizes of 1,000 particles.

[Bonding of Biological Substance Recognition Site and Fluorescent Substance-Containing Nanoparticles]

The biological substance recognition site of the embodiment is a site which specifically bonds and/or reacts with a target biological substance. The target biological substance is not particularly limited as long as there is a substance which specifically bonds therewith. Representative examples thereof include a protein (e.g. peptide), a nucleic acid (e.g. oligonucleotide and polynucleotide) and an antibody. Therefore, examples of the substance which bonds with such a target biological substance include: an antibody which recognizes the above protein as an antigen; another protein which specifically bonds with the above protein; and a nucleic acid having a base sequence which is hybridized with the above nucleic acid. Specific examples thereof include: an anti HER2 antibody which specifically bonds with HER2, which is a protein present on the surface of a cell; an anti ER antibody which specifically bonds with an estrogen receptor (ER) present on a cell nucleus; and an anti actin antibody which specifically bonds with actin, which forms a cytoskeleton. The fluorescent substance-containing nanoparticles bonding with the anti HER2 antibody and the anti ER antibody are particularly preferable because they can be used in selecting medication for breast cancer.7

The form of bonding of the biological substance recognition site and the fluorescent substance-containing nanoparticles is not particularly limited. Examples thereof include covalent bonding, ionic bonding, hydrogen bonding, coordinate bonding, physical adsorption and chemical adsorption. For stability of bonding, bonding with strong bonding force such as covalent bonding is preferable.

There may be an organic molecule(s) which connects the biological substance recognition site with the fluorescent substance-containing nanoparticles. For example, in order to prevent non-specific adsorption to a biological substance, a polyethyleneglycol chain can be used, and SM (PEG)12 produced by Thermo Scientific can be used.

When the biological substance recognition site is bonded to fluorescent substance-containing silica nanoparticles, regardless of whether the fluorescent substance is a fluorescent organic dye or a quantum dot, the same procedure can be applied. For example, a silane coupling agent, which is a compound widely used for bonding an inorganic material and an organic material, can be used. The silane coupling agent is a compound having an alkoxysilyl group providing a silanol group by hydrolysis at one end of the molecule and a functional group, such as a carboxy group, an amino group, an epoxy group or an aldehyde group, at the other end thereof, and bonds with an inorganic material through an oxygen atom of the silanol group. Specific examples thereof include mercaptopropyl triethoxysilane, glycidoxypropyl triethoxysilane, aminopropyl triethoxysilane, and a silane coupling agent having a polyethylene glycol chain (e.g. PEG-silane no. SIM6492.7 produced by Gelest, Inc.). When the silane coupling agent is used, two or more types thereof may be used together.

As the procedure of reacting fluorescent organic dye-containing silica nanoparticles and a silane coupling agent, a well-known method can be used. For example, fluorescent organic dye-containing silica nanoparticles obtained are dispersed in pure water, aminopropyl triethoxysilane is added thereto, and reaction is performed at room temperature for 12 hours. After the reaction ends, by centrifugation or filtration, fluorescent organic dye-containing silica nanoparticles having the surface modified with the aminopropyl group can be obtained. Next, the amino group is reacted with the carboxy group in an antibody so that the antibody can bond with the fluorescent organic dye-containing silica nanoparticles through amide bonding. A condensing agent such as EDC (1-Ethyl-3-[3-Dimethylaminopropyl]carbodiimide Hydrochloride: Pierce®) can also be used as needed.

A linker compound having a site which can directly bond with the fluorescent organic dye-containing silica nanoparticles modified with an organic molecule and a site which can bond with the molecule target substance can be used as needed. For example, when sulfo-SMCC (Sulfosuccinimidyl 4[N-maleimidomethyl]-cyclohexane-1-carboxylate: Pierce) having both a site which selectively reacts with an amino group and a site which selectively reacts with a mercapto group is used, the amino group of the fluorescent organic dye-containing silica nanoparticles modified with aminopropyl triethoxysilane and the mercapto group in the antibody are bonded, whereby the fluorescent organic dye-containing silica nanoparticles bonding with the antibody can be produced.

When the biological substance recognition site is bonded to fluorescent substance-containing polystyrene nanoparticles, regardless of whether the fluorescent substance is a fluorescent organic dye or a quantum dot, the same procedure can be applied. In other words, impregnation of a fluorescent organic dye or a quantum dot into polystyrene nanoparticles having a functional group such as an amino group can produce fluorescent substance-containing polystyrene nanoparticles having the functional group, and use of EDC or sulfo-SMCC thereafter can produce fluorescent substance-containing polystyrene nanoparticles bonding with an antibody.

Examples of the antibody which recognizes a specific antigen include M. actin, M.S. actin, S.M. actin, ACTH, Alk-1, α1-antichymotrypsin, α1-antitrypsin, AFP, bcl-2, bcl-6, β-catenin, BCA 225, CA19-9, CA125, calcitonin, calretinin, CD1a, CD3, CD4, CD5, CD8, CD10, CD15, CD20, CD21, CD23, CD30, CD31, CD34, CD43, CD45, CD45R, CD56, CD57, CD61, CD68, CD79a, "CD99, MIC2", CD138, chromogranin, c-KIT, c-MET, collagen type IV, Cox-2, cyclin D1, keratin, cytokeratin (high molecular mass), pankeratin, pankeratin, cytokeratin 5/6, cytokeratin 7, cytokeratin 8, cytokeratin 8/18, cytokeratin 14, cytokeratin 19, cytokeratin 20, CMV, E-cadherin, EGFR, ER, EMA, EBV, factor VIII-related antigen, fassin, FSH, galectin-3, gastrin, GFAP, glucagon, glycophorin A, granzyme B, hCG, hGH, *helicobacter pyroli*, HBc antigen, HBs antigen, hepatocyte specific antigen, HER2, HSV-I, HSV-II, HHV-8, IgA, IgG, IgM, IGF-1R, inhibin, insulin, kappa L chain, Ki67, lambda L chain, LH, lysozyme, macrophage, melan A, MLH-1, MSH-2, myeloperoxidase, myogenin, myoglobin, myosin, neurofilament, NSE, p27 (Kip1), p53, p53, P63, PAX 5, PLAP, *pneumocystis carinii*, podoplanin (D2-40), PGR, prolactin, PSA, prostatic acid phosphatase, Renal Cell Carcinoma, S100, somatostatin, spectrin, synaptophysin, TAG-72, TdT, cycloglobulin, TSH, TTF-1, TRAcP, tryptase, villin, vimentin, WT1 and Zap-70.

[Staining Method]

Hereinafter, the staining method of tissue sections is described. The staining method described below is applicable not only to pathological sections of tissue but also to cells. Further, the method of producing sections to which the staining method described below is applicable is not particularly limited, and sections produces by a well-known method can be used.

1) Deparaffinization

A pathological section is immersed in a container containing xylene so that paraffin is removed. The temperature is not particularly limited, and the processing can be performed at room temperature. Preferably, the immersing time is 3 minutes or more and 30 minutes or less. The xylene may be changed during the immersion as needed.

Next, the pathological section is immersed in a container containing ethanol so that the xylene is removed. The temperature is not particularly limited, and the processing can be performed at room temperature. Preferably, the immersing time is 3 minutes or more and 30 minutes or less. The ethanol may be changed during the immersion as needed.

Next, the pathological section is immersed in a container containing water so that the ethanol is removed. The temperature is not particularly limited, and the processing can be performed at room temperature. Preferably, the immersing time is 3 minutes or more and 30 minutes or less. The water may be changed during the immersion as needed.

2) Activation Processing

Activation processing of a target biological substance is performed in conformity with a well-known method. Although the activation conditions are not specifically determined, as an activation liquid, 0.01M citric acid buffer solution (pH 6.0), 1 mM EDTA solution (pH 8.0), 5% urea, 0.1M tris-hydrochloric acid buffer solution or the like can be used, and as a heating device, an autoclave, a microwave, a pressure pan, a water bath or the like can be used. The temperature is not particularly limited, and the processing can be performed at room temperature. The temperature may be 50 to 130° C., and the activating time may be 5 to 30 minutes.

Next, the activated section is immersed in a container containing PBS (Phosphate Buffered Saline) so as to be washed. The temperature is not particularly limited, and the processing can be performed at room temperature. Preferably, the immersing time is 3 minutes or more and 30 minutes or less. The PBS may be changed during the immersion as needed.

3) Staining with Fluorescent Substance-Containing Nanoparticles Bonding with Biological Substance Recognition Site A PBS dispersion of fluorescent substance-containing nanoparticles bonding with a biological substance recognition site is put on the pathological section so as to be reacted with the target biological substance. By changing the biological substance recognition site, which is bonded to the fluorescent substance-containing nanoparticles, to another, staining for a variety of biological substances becomes available. When fluorescent substance-containing nanoparticles bonding with multiple types of the biological substance recognition site are used, PBS dispersions of the respective fluorescent substance-containing nanoparticles may be mixed in advance, or individually and successively put on the pathological section.

The temperature is not particularly limited, and the processing can be performed at room temperature. Preferably, the reacting time is 30 minutes or more and 24 hours or less.

Preferably, a well-known blocking agent such as BSA-containing PBS is dripped before staining with the fluorescent substance-containing nanoparticles is performed.

Next, the stained section is immersed in a container containing PBS so that the unreacted fluorescent substance-containing nanoparticles are removed. The temperature is not particularly limited, and the processing can be performed at room temperature. Preferably, the immersing time is 3 minutes or more and 30 minutes or less. The PBS may be changed during the immersion as needed. A cover glass is placed on the section to seal. A commercially available sealing agent may be used as needed.

When staining with an HE staining reagent is performed, the HE staining is performed before sealing with the cover glass is performed.

[Acquisition of Fluorescence Image]

The microscopic image acquisition device 1A is used on the stained pathological section so as to acquire a microscopic image (fluorescence image) with a wide field. In the microscopic image acquisition device 1A, an excitation light source and an optical filter for fluorescence detection suitable for the wavelength of maximum absorption of the fluorescent substance and the fluorescence wavelength thereof used in the staining reagent are selected.

The field for a fluorescence image(s) is preferably 3 mm$^2$ or more, far preferably 30 mm$^2$ or more and still far preferably 300 mm$^2$ or more.

<Operation of Pathological Diagnosis Support System 100 (Image Processing Method Included)>

Hereinafter, operation of the pathological diagnosis support system 100 to acquire and analyze the above-described fluorescence image and bright field image is described. Here, a tissue section stained with a staining reagent containing fluorescent substance-containing nanoparticles bonding with a biological substance recognition site which recognizes a specific protein (here, Ki67 protein in breast cancer tissue, hereinafter called a "specific protein") is an observation target. However, the observation target is not limited thereto.

First, an operator stains a tissue section with two types of staining reagents, the hematoxylin staining reagent and the staining reagent of, as a fluorescence labeling material, fluorescent substance-containing nanoparticles bonding with a biological substance recognition site which recognizes a specific protein.

Thereafter, a bright field image and a fluorescence image are acquired in the microscopic image acquisition device 1A by the procedure of Steps (a1) to (a5).

(a1) Place on a slide the tissue section stained with the hematoxylin staining reagent and the staining reagent of the fluorescent substance-containing nanoparticles bonding with the biological substance recognition site which recognizes the specific protein and set the slide on the slide fixing stage of the microscopic image acquisition device 1A by an operator.

(a2) Set the bright field unit, adjust the capturing magnification and the focus, and position the region of the observation target on the tissue in the field.

(a3) Perform capturing with the imaging unit so as to generate image data of a bright field image, and send the image data to the image processing device 2A.

(a4) Change the unit to the fluorescence unit.

(a5) Perform capturing with the imaging unit without changing the field and the capturing magnification so as to generate image data of a fluorescence image, and send the image data to the image processing device 2A.

The image processing device 2A performs the image analysis processing based on a bright field image and a fluorescence image.

Figure 5:
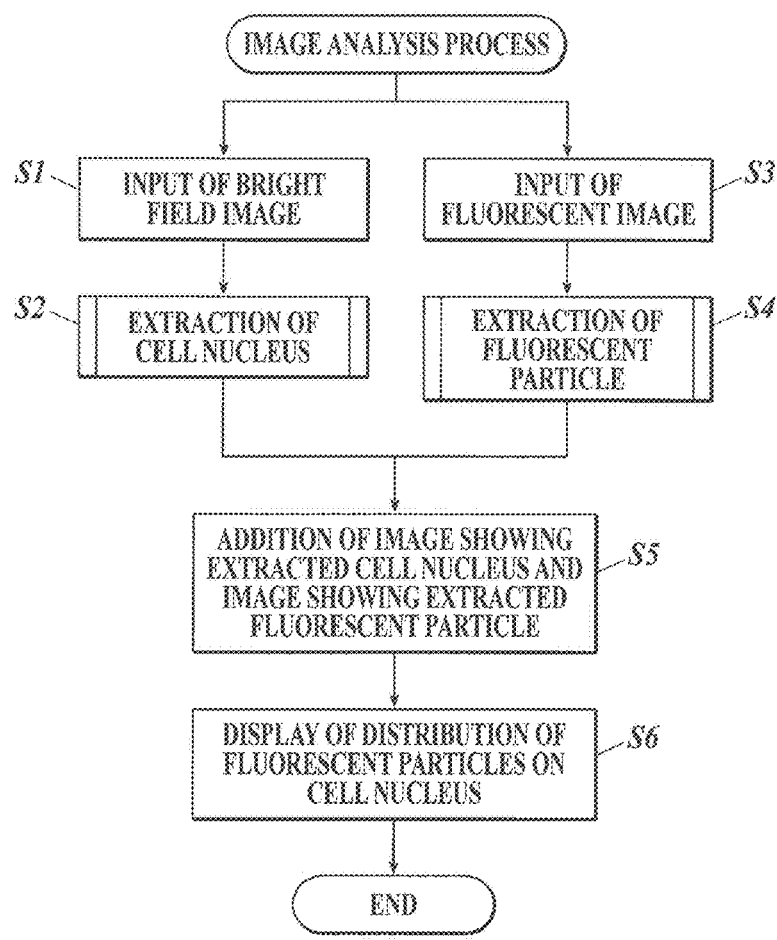
FIG. 5 is a flowchart showing an image analysis processing performed by a control unit shown in FIG. 2.

FIG. 5 shows a flowchart of the image analysis processing performed in the image processing device 2A. The image analysis processing shown in FIG. 5 is performed by the control unit 21 working together with a program(s) stored in the storage unit 25.

When a bright field image is input from the microscopic image acquisition device 1A through the communication I/F 24 (Step S1), the regions of cell nuclei are extracted from the bright field image (Step S2).

Figure 6:
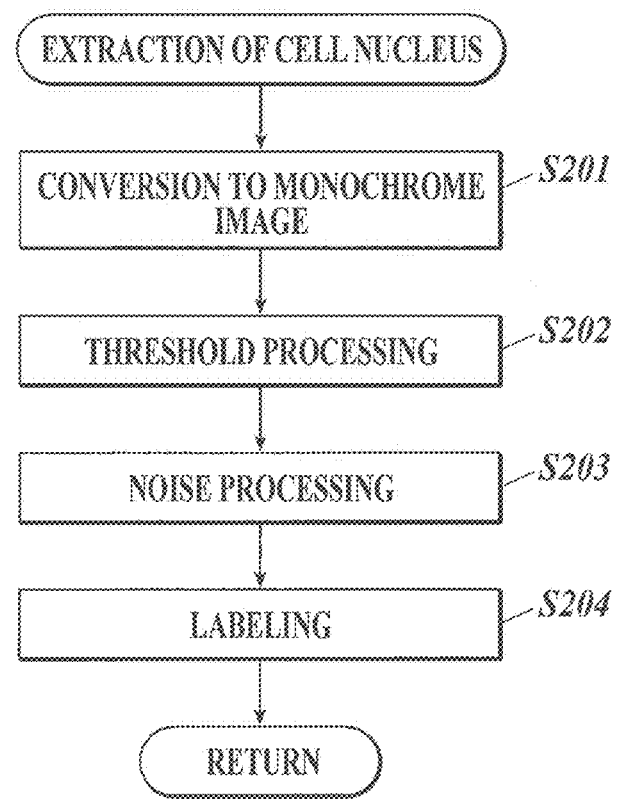
FIG. 6 is a flowchart showing details of processing of Step S2 in FIG. 5.

FIG. 6 shows the detailed flow of the processing of Step S2. The processing of Step S2 is performed by the control unit 21 working together with the program stored in the storage unit 25.

Figure 7A:
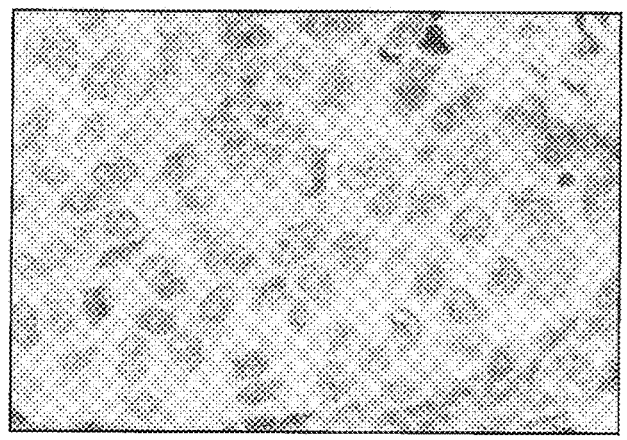
FIG. 7A shows a bright field image.

At Step S2, first, the bright field image is converted to a monochrome image (Step S201). FIG. 7A shows an example of bright field image.

Next, threshold processing is performed on the monochrome image using a predetermined threshold value so as to binarize values of pixels thereof (Step S202).

Figure 7B:
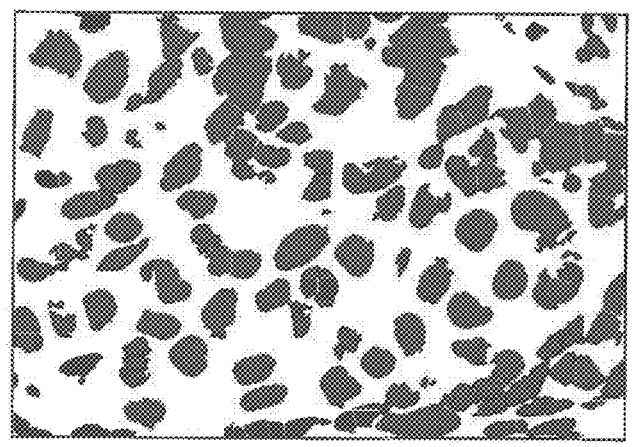
FIG. 7B shows an image showing extracted cell nuclei.

Next, noise processing is performed (Step S203). More specifically, noise processing can be performed by closing on the binary image. Closing is processing of performing dilation and then erosion the same number of times. Dilation is processing of replacing a pixel of interest with white when any of the pixels in a region of n×n pixels (n is an integer of 2 or more) from the pixel of interest is white. Erosion is processing of replacing the pixel of interest with black when any of the pixels in the region of n×n pixels from the pixel of interest is black. Closing can remove small regions such as noise. FIG. 7B shows an example of noise-processed image. As shown in FIG. 7B, after noise processing, an image (cell nucleus image) with cell nuclei extracted can be generated.

Next, labeling is performed on the noise-processed image, thereby attaching a label to each of the extracted cell nuclei (Step S204). Labeling is processing of attaching the same label (number) to pixels connected to each other so as to identify an object in an image. Labeling make it possible to identify the cell nuclei in the noise-processed image and attach labels thereto.

On the other hand, when a fluorescence image is input from the microscopic image acquisition device 1A through the communication I/F 24 (Step S4), fluorescent substance-containing nanoparticles (hereinafter, called "fluorescent particles" in the present embodiments) are extracted from the fluorescence image (Step S4).

FIG. 8 shows the detailed flow of the processing of Step S4. The processing of Step S4 is performed by the control unit 21 working together with the program stored in the storage unit 25.

In Step S4, a color component is extracted according to the wavelength of the fluorescent bright points from the fluorescent image (step S401)

Figure 9A:
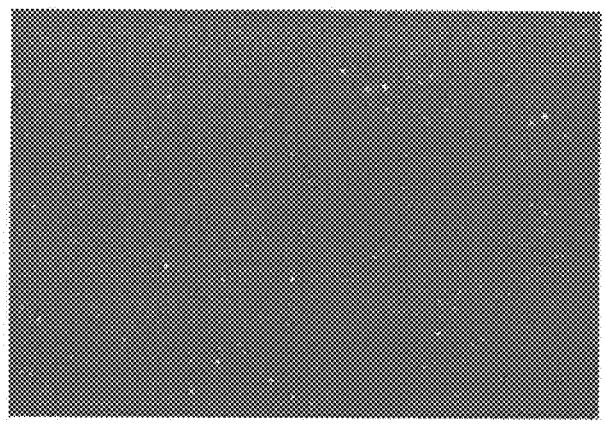
FIG. 9A shows a fluorescence image.

FIG. 9A shows an example of a fluorescence image.

In step S301, when the emission wavelength of the fluorescent substance included nanoparticle is 550 nm, for example, only the fluorescent bright points having the wavelength are extracted as an image.

Next, threshold processing is performed on the extracted image to generate a binary image and to extract bright point regions (step S402).

Before the threshold processing, noise removal processing can be performed to remove the autofluorescence of the cell, other components due to unnecessary signals, etc. A low-pass filter such as a Gaussian filter and a high-pass filter such as a secondary differential filter are preferably used.

Figure 9B:
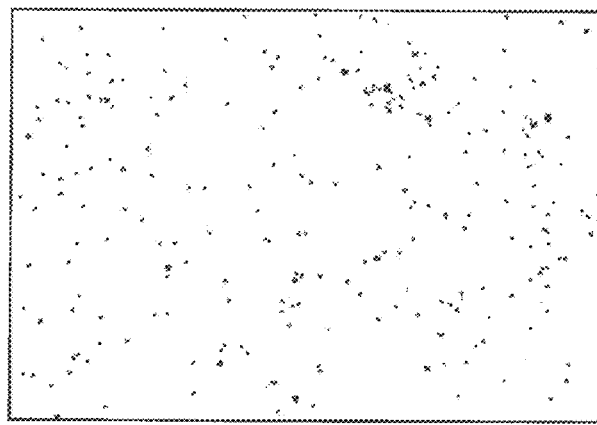
FIG. 9B is an image showing extracted regions of bright points.

FIG. 9.B is an image showing extracted bright point regions. As shown in FIG. 9B, each of the extracted images of bright point regions has a fluorescent bright point at its center.

Next, the image showing extracted bright point regions and the fluorescent image are added and a luminance profile is generated by mapping the luminance signal in each of the bright point regions (Step S403). The number and the locations of fluorescent particles within each bright point region are calculated on the basis of the luminance profile (Step S404).

A "luminance profile" provides information of two-dimensional distribution of luminance signal based on the image extracted from a fluorescence image masked with an image showing extracted bright point regions, that is, the value and position (the spread of luminance signal) of luminance signal in each of the bright point regions.

As shown in FIG. 10, when an image showing extracted bright point regions is generated from a fluorescence image (FIG. 10A), the image showing an extracted bright point region (FIG. 10B which corresponds to the region enclosed with a square flame in FIG. 10A) and the fluorescence image in the bright point region (FIG. 10C) are superimposed for each bright point region. A second fluorescence image (FIG. 10D) corresponding to the bright point region is generated from the fluorescence image using the image showing the extracted bright point region as a mask. A luminance profile is the distribution of luminance in each location defined by an x coordinate and a y coordinate (FIG. 10E), which is prepared on the basis of the second fluorescence image.

In fact, one or plural fluorescent particles are included in one bright point region. Accordingly, the luminance profile shows the luminance and position depending on the number of fluorescent particles and the position of each fluorescent particle. The number of fluorescent particles and the position of each fluorescent particle in the bright point region are calculated from the luminance profile.

Figure 10A:
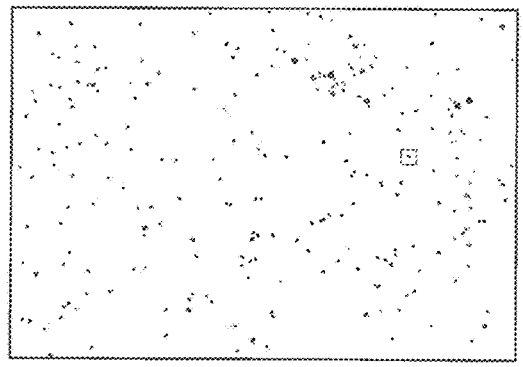
FIG. 10A is an image showing bright point regions extracted from a fluorescence image for schematically illustrating the generation processing of luminance profile.
Figure 10B:
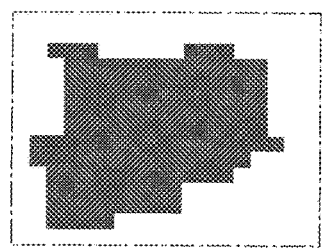
FIG. 10B is an enlarged image showing an extracted bright point region for schematically illustrating the generation processing of luminance profile.
Figure 10C:
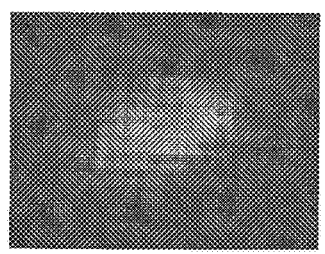
FIG. 10C is a fluorescence image corresponding to the extracted bright point region for schematically illustrating the generation processing of luminance profile.
Figure 10D:
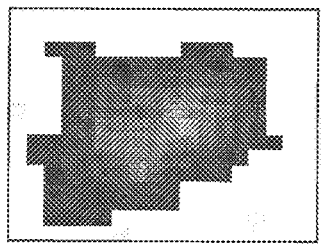
FIG. 10D is a mask-processed fluorescence image corresponding to the extracted bright point region for schematically illustrating the generation processing of luminance profile.
Figures 10E, 10F:
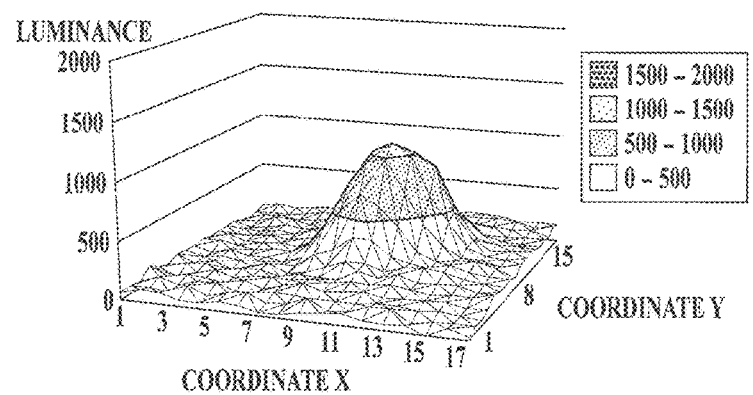
FIG. 10E is an image showing a luminance profile which expresses the distribution of luminance two dimensionally, in the location defined by an x coordinate and a y coordinate.
FIG. 10F is an image showing a luminance profile which expresses the distribution of luminance three dimensionally, in the location defined by an x coordinate and a y coordinate.

The luminance profile may be two-dimensionally expressed luminance in the location defined by an x coordinate and a y coordinate as shown in FIG. 10E. Otherwise, it may be three-dimensionally expressed luminance, the luminance (height) in the location defined by an x coordinate (horizontal axis) and a y coordinate (vertical axis) as shown in FIG. 10F. The three-dimensionally expressed luminance profile as shown in FIG. 10F can be easily recognized and is used in the following descriptions.

In the embodiment, the luminance profile according to one fluorescence particle is prepared in advance from a single fluorescence particle captured under the same condition as in capturing the input fluorescence image. The number and the coordinate location of fluorescent particle for the luminance profile are set as the initial value (reference).

Figure 11A:
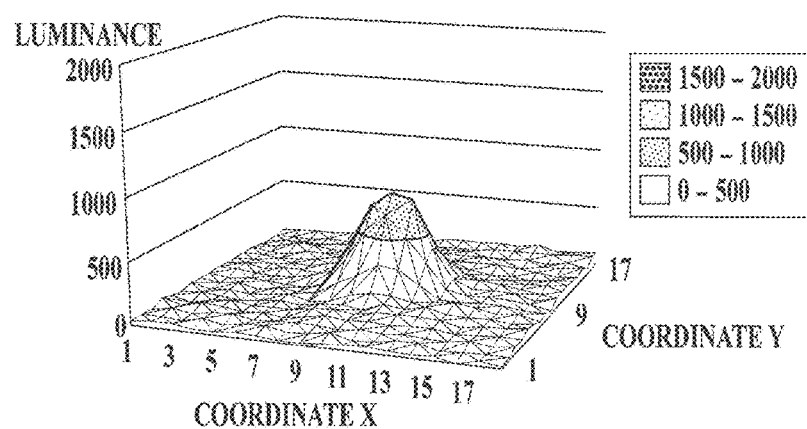
FIG. 11A is an image showing a luminance profile (reference profile) of one fluorescent particle.
Figure 11B:
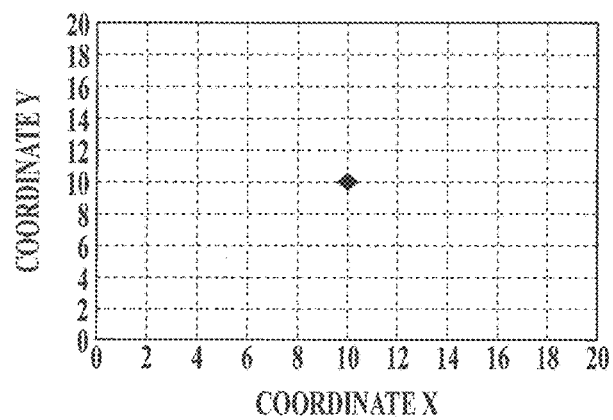
FIG. 11B shows the calculation results (number of fluorescent particle and location of fluorescent particle defined by an x coordinate and a y coordinate) according to the luminance profile in FIG. 11A.

FIG. 11A is an example of an image showing a luminance profile of one fluorescent particle. FIG. 11B shows the results (the number of fluorescent particle and the location of the fluorescent particle defined by an x coordinate and a y coordinate) calculated on the basis of the luminance profile.

The luminance profile of one fluorescent particle prepared in advance is set as a "reference profile" and is compared with the luminance profile of each bright point region in Step S404. The number of fluorescent particles and the location of each fluorescent particle in each bright point region are calculated in Step S404.

For example, consider the case where the reference profile in FIG. 11A is prepared in advance, the information (the number and the coordinate location) of fluorescent particle in FIG. 11B is set, and luminance profiles in FIG. 12A, FIG. 12C, FIG. 13A, and FIG. 13B are generated.

In that case, the reference profile in FIG. 11A is compared with the luminance profiles in FIG. 12A, FIG. 12C, FIG. 13A, and FIG. 13B. The information (the number and the coordinate location) of the fluorescent particles is calculated on the basis of the luminance (height of the peak) and the position (spread or slope around the peak) according to the reference profile.

Figure 12A:
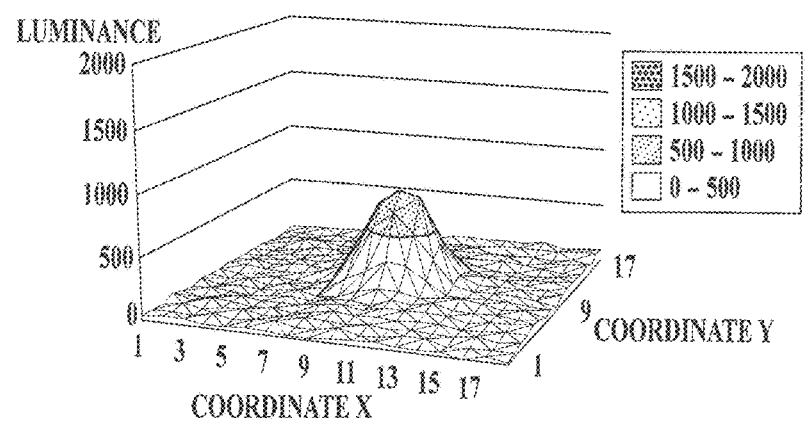
FIG. 12A is an image showing a luminance profile of one fluorescent particle.
Figure 12B:
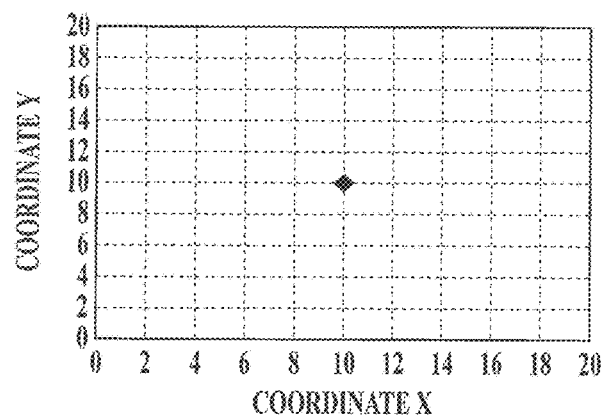
FIG. 12B is an image showing the number and the coordinate location of one fluorescent particle.

The height of the peak and the spread and slope around the peak in the luminance profile in FIG. 12A match those in the reference profile. Thus, it is determined that one fluorescent particle exists alone, as shown in FIG. 12B.

Figure 12C:
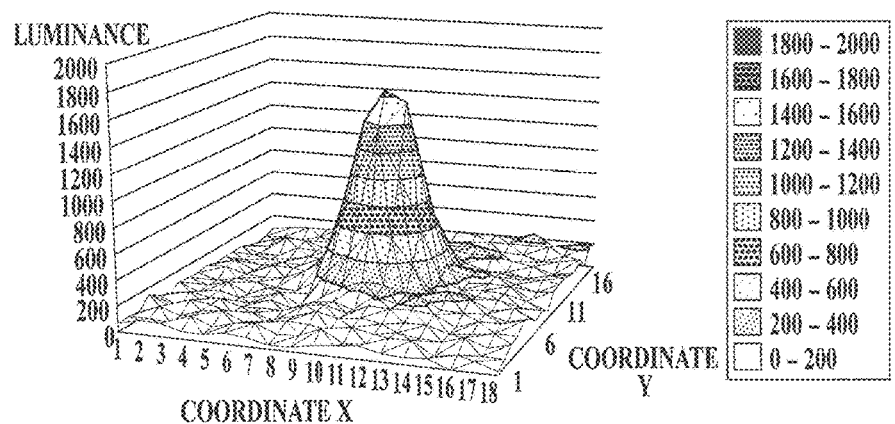
FIG. 12C is an image showing a luminance profile of two fluorescent particles.
Figure 12D:
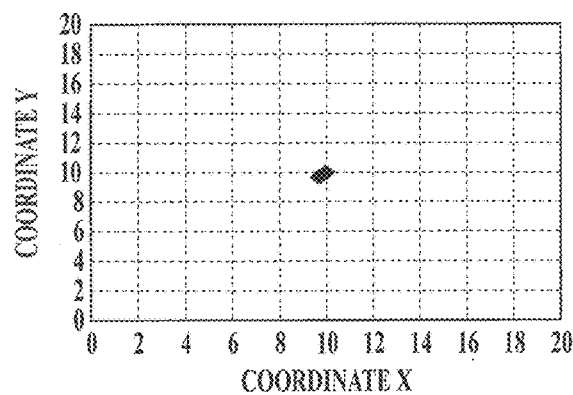
FIG. 12D is an image showing the number and the coordinate locations of two fluorescent particles.

According to the high peak and the steep slope around the peak in the luminance profile in FIG. 12C, it is determined that two fluorescent particles exist close to each other as shown in FIG. 12D.

Figure 13A:
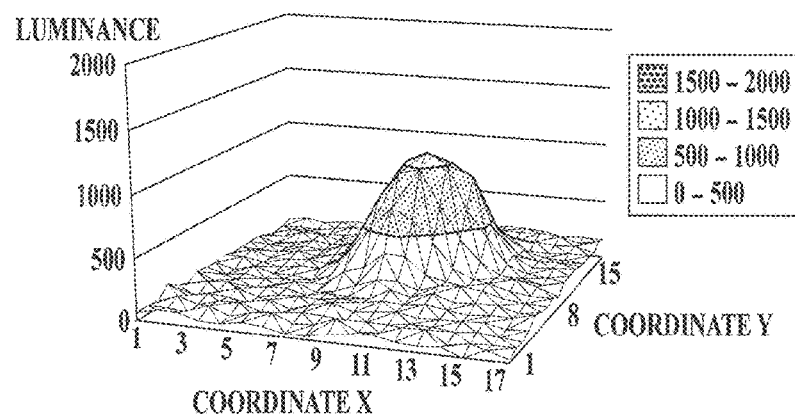
FIG. 13A is an image showing a luminance profile of three fluorescent particles.
Figure 13B:
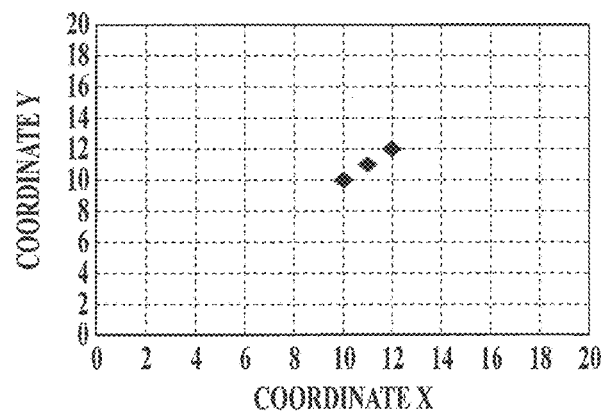
FIG. 13B is an image showing the number and the coordinate locations of three fluorescent particles.

According to the high peak in the luminance profile and a certain range of the spread around the peak in FIG. 13A, it is determined that three fluorescent particles exist almost at equal intervals as shown in FIG. 13B.

Figure 13C:
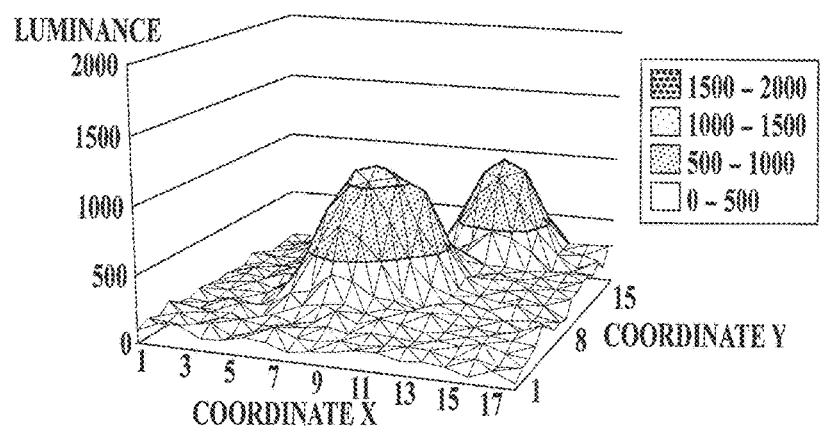
FIG. 13C is an image showing a luminance profile of three fluorescent particles.
Figure 13D:
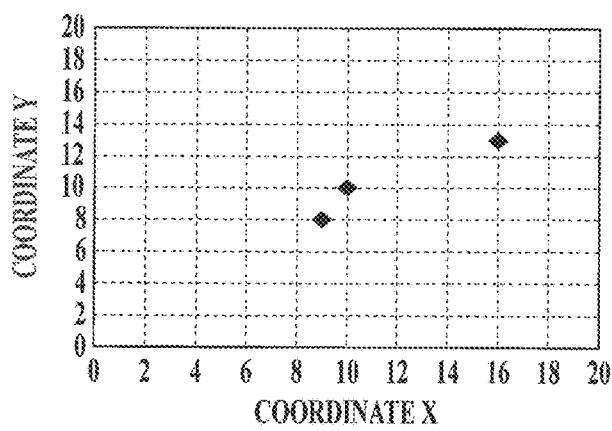
FIG. 13D is an image showing the number and the coordinate locations of three fluorescent particles.

There are two peaks in the luminance profile in FIG. 13A; one being high and broad, the other having the height and spread which are the same as those in the reference profile. It is determined that three fluorescent particles exist as shown in FIG. 13D; two of them exist at a certain interval and the remaining one fluorescent particle exists alone at a distance.

As shown above, the number of the fluorescent particles and the position of each fluorescent particle in a bright point region can be determined easily even when there exist plural fluorescent particles, provided that a reference profile is prepared and the number and the coordinate location of the fluorescent particles are set in advance.

Figure 9C:
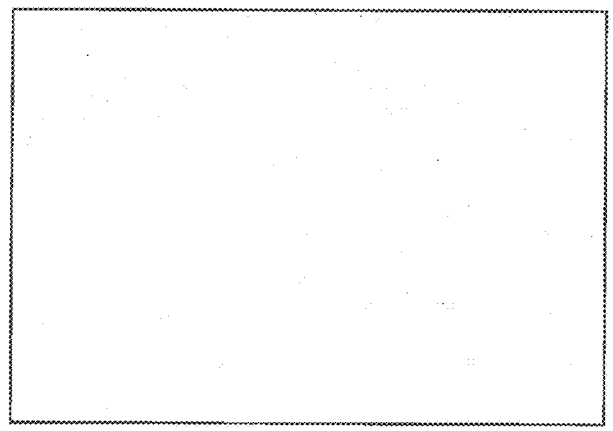
FIG. 9C is an image showing extracted fluorescent particles.

The number of the fluorescent particles and the location of each fluorescent particle in each bright point region are shown in FIG. 9C, which is an image showing extracted fluorescent particles (fluorescent particle image).

The number and the location of fluorescent particles are determined using a luminance profile of one fluorescent particle as a reference profile. The number and the location of fluorescent particles can also be determined using a reference profile which is a luminance profile of plural fluorescent particles prepared in advance. The number and the location of fluorescent particles can also be determined by decomposing the luminance profile made from plural fluorescent particles using a two-dimensional Fourier transform and the like.

Next, labeling processing is performed on the fluorescent particle image, thereby attaching a label to each of the extracted fluorescent particles (Step S405).

After the processing of Step S2 and S4, the control section 21 returns to the processing shown in FIG. 5 and performs addition processing of the cell nucleus image (see FIG. 7B) and the fluorescent particle image (see FIG. 9C), to show the distribution of fluorescent particles on cell nuclei (step S6).

Figure 14:
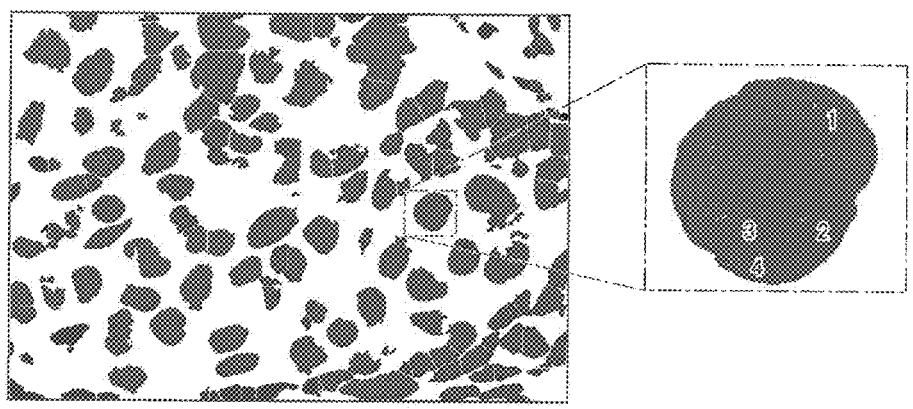
FIG. 14 is a superimposed image of an image showing extracted cell nuclei and an image showing extracted fluorescent particles.

FIG. 14 is an example of a superimposed image after addition processing.

Figure 15:
FIG. 15 is an image showing distribution of fluorescent particles on a cell nucleus.

FIG. 15 is an example of an image showing distribution of fluorescent particles on a cell nucleus.

As shown in FIG. 14, the extracted fluorescent particles are superimposed on the extracted cell nuclei by the addition processing of the cell nucleus image and the fluorescent particle image. As a result, fluorescent particles in each bright point region are displayed on each cell nucleus, as in the magnified image in FIG. 14. According to the magnified image in FIG. 14, one fluorescent particle extracted from the luminance profile in FIG. 12A are displayed as "1", two fluorescent particles extracted from the luminance profile in FIG. 12C are displayed as "2", three fluorescent particles extracted from the luminance profile in FIG. 13A are displayed as "3", and three fluorescent particles extracted from the luminance profile in FIG. 13C are displayed as "4".

The actual image corresponding to the magnified image in FIG. 14 is displayed on a display section 23 as shown in FIG. 15. The distribution, the number of the fluorescent particles and the position of each fluorescent particle on a specific site (cell nucleus) in the cell of the observation target, can be specifically displayed and recognized. The number of the fluorescent particles and the position of each fluorescent particle (distribution) overlapping the cell nuclei show the expression state of the specific protein as an indicator of the grade or stage of cancer.

Figure 16:
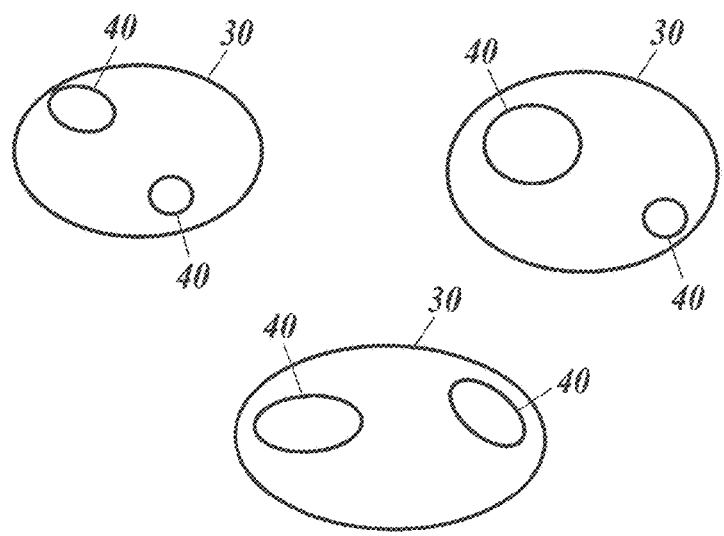
FIG. 16 is a schematic image showing extracted bright points when fluorescent particles of one type are used.
Figure 17:
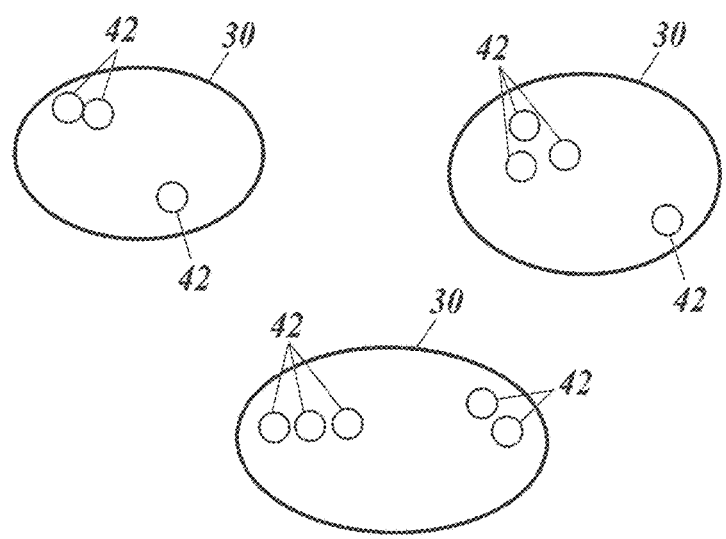
FIG. 17 is a schematic image showing extracted bright points when fluorescent particles of one type are used.

According to the above embodiment, as shown in FIG. 16, cell nuclei 30 are extracted by the processing in Steps S1-S2; bright point regions 40 are extracted by the processing in Steps S3-S4 (S401-S402); and the distribution of the fluorescent particles 42 on cell nuclei 30 can be specifically displayed and recognized by the processing in Steps S403-S404.

Accordingly, the expression (the number and the location) of a specific protein in the observation target cell can be easily and accurately quantitated. This enables to quantitate biological substances and to evaluate the location of biological substances in the observation target cell accurately, which have been difficult to analyze from the conventional fluorescent bright point image. The location of biological substances in a cell is estimated to relate to the grade of cancer such as infiltration and stage. The visualization of the metastasis of cancer and activity of cancer as shown in the embodiment is considered to contribute to cancer prevention and decision of a course of cancer treatment.

The described contents in the above embodiment are preferred examples of the present invention, and the present invention is not limited thereto.

For example, in the above embodiment, as an example of the specific protein, Ki67 protein in breast cancer is cited, but the specific protein is not limited thereto. By changing type of the biological substance recognition site, which is used to acquire a fluorescence image(s), to another suitable for a lesion (cancer) type as a diagnosis target, the feature amount quantitatively showing the amount of expression of a specific protein for the lesion type can be provided for a doctor.

In the above embodiment, the specific protein of only one type was the target. Two or more types of fluorescent particles having different emission wavelength from each other can be used for plural types of specific proteins.

In this case, each color component is extracted using a filter and the like in Step S401; the processing in Steps S402-S405 are performed for each color component (wavelength component); and the cell nucleus image and the fluorescent particle image generated for each color component is added in Step S5. As a result, the distribution of fluorescent particles is displayed for each type of fluorescent particles (for each specific protein) in Step S6. In addition to the expression state of the specific protein in cell nuclei, the closeness of each specific protein can also be displayed.

Figure 18:
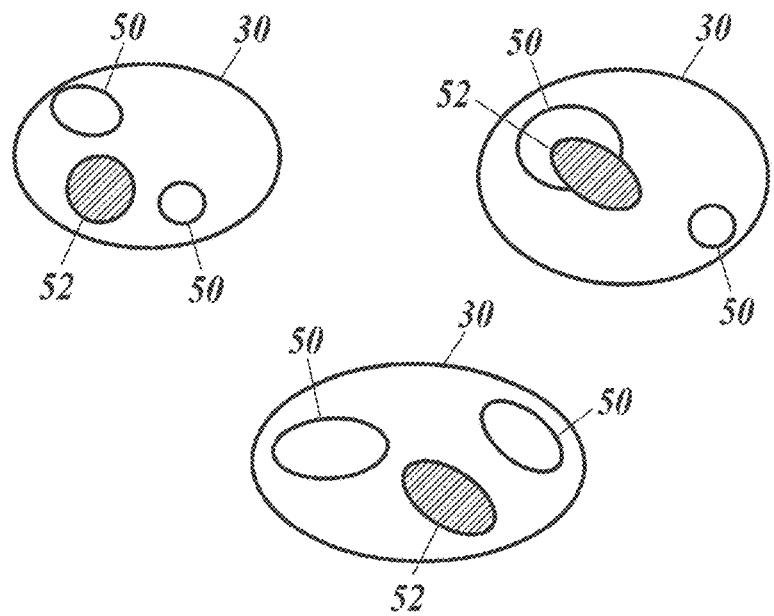
FIG. 18 is a schematic image showing extracted bright points when fluorescent particles of two types are used.
Figure 19:
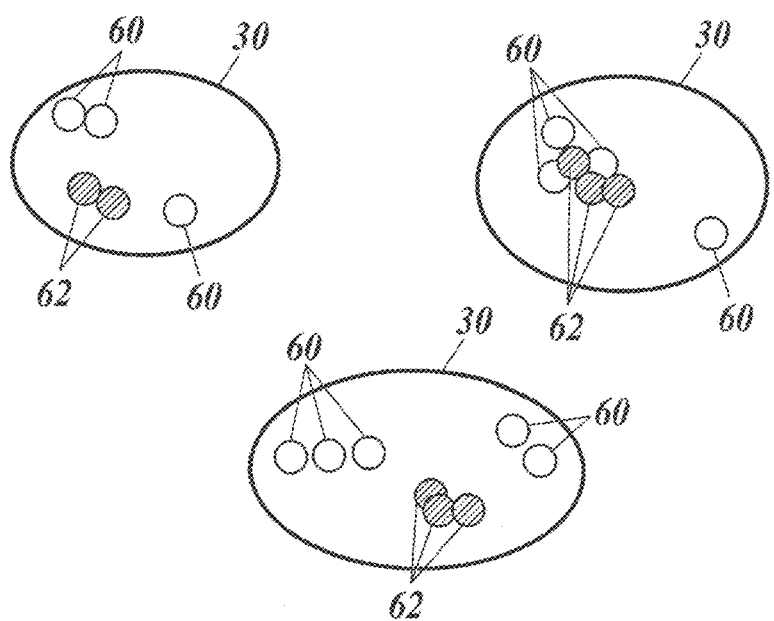
FIG. 19 is a schematic image showing extracted bright points when fluorescent particles of two types are used.

According to the processing, as shown in FIG. 18, cell nuclei 30 are extracted by the processing in Steps S1-S2; bright point regions 50 and 52 are extracted by the processing in Steps S3-S4 (S401-S402); and, as shown in FIG. 19, the distribution of the fluorescent particles 60 and 62 can be displayed for each specific protein by the processing in Steps S403-S404.

Further, in the above, as a computer readable medium of the programs of the present invention, an HDD, a nonvolatile semiconductor memory or the like is used as an example, but the present invention is not limited thereto. As another computer readable medium, a portable storage medium such as a CD-ROM can be used. Further, as a medium to provide data of the programs of the present invention, a carrier wave can be used.

Besides, the detailed configurations and detailed operations of the devices constituting the pathological diagnosis support system 100 can also be appropriately modified within the scope not departing from the spirit of the present invention.

Example 1

(A) Preparation of Staining Reagent (a)
(A-1) Preparation of Fluorescent Substance-Containing Nanoparticles (Nanoparticle 1; Red Melamine Particle)

14.4 mg of SulfoRhodamine101 (available from Sigma-Aldrich Corporation), which is a red light emitting dye used as a fluorescent dye, was dissolved in 22 ml of water. To the solution was added 2 ml of 5% aqueous solution of Emulsion® 430 (polyoxyethylene oleyl ether, available from Kao Corporation), which is an emulsion for emulsion polymerization. After heating to 70° C. during stirring on a hot stirrer, 0.65 g of Nikalac MX-035 (manufactured by Nippon Carbide Industries Co., Inc.), which is a raw material of melamine resin, was added to the solution.

Next, 1000 µL of 10% aqueous solution of dodecylbenzenesulfonic acid (available from Kanto Chemical Co., Inc.) as a surfactant was added to the solution and was stirred for 50 minutes at 70° C. Thereafter, the solution was further stirred for 20 minutes after heating to 90° C. The obtained particle dispersion of dye and resin was washed with pure water in order to remove impurities such as excess raw materials of resin and fluorescent dye.

Specifically, the dispersion was centrifuged at 20,000 G for 15 minutes with a Centrifugal separator (Micro Refrigerated Centrifuge 3740 by Kubota Corp.) followed by removal of supernatant and re-dispersion by addition of extra pure water and ultrasonic irradiation. The centrifugation, removal of supernatant, and re-dispersion were repeated five times. The obtained melamine particles were positively charged, due to a lot of amino groups in the skeleton of the melamine resin. The evaluation of charge of the resin particles was performed by component analysis of resin by NMR, IR, and the like, and by measurement of zeta potential.

The obtained nanoparticles bonded with dye were adjusted to 3 nM by using PBS (Phosphate Buffered Saline) containing 2 mM of EDTA (ethylenediaminetetraacetic acid). The solution was mixed with SM (PEG) 12 (Thermo Scientific, succinimidyl-[(N-maleomidopropionamid)-dodecaethyleneglycol]ester) so as to be a final concentration of 10 mM, and make it react for 1 hour. The reacted mixture was centrifuged at 10,000 G for 20 minutes, and the supernatant was removed. PBS containing 2 mM of EDTA was added so as to disperse the precipitates and centrifugation was performed again. The same procedures for washing were repeated three times, to obtain nanoparticles containing a fluorescent dye having a maleimide group at an end.

On the other hand, a solution of streptavidin which can bind to the maleimide group of the nanoparticles containing a fluorescent dye was obtained by adding thiol group to streptavidin (available from Wako Pure Chemical Industries, Ltd.) using N-succinimidyl S-acetylthioacetate (SATA) followed by filtration using a gel filtration column.

The nanoparticles containing a fluorescent dye having a maleimide group at an end and the streptavidin described above were mixed in PBS containing 2 mM of EDTA and make it react for 1 hour. 10 mM of mercaptoethanol was added so as to end the reaction. After concentration of the obtained solution by centrifugation and filtration, the unreacted streptavidin and the like were removed using a gel filtration column for purification, to finally obtain red melamine nanoparticles bonded with SulfoRhodamine further bonded with streptavidin (nanoparticles 1).

The nanoparticles 1 were observed under a scanning electron microscope (SEM; S-800 by Hitachi®, Ltd.) and had an average particle size of 150 nm and a variation coefficient of 12%.

(A-2) [Bonding of Antibody to Fluorescent Substance-Containing Nanoparticles]

An antibody was bonded to the fluorescent substance-containing nanoparticles by the method of the following Steps (1) to (12).

Step (1): Disperse 1 mg of the nanoparticles 1 in 5 mL of pure water. Next, add 100 μL of an aminopropyltriethoxysilane aqueous dispersion (LS-3150; Manufactured by Shinetsu Kagaku Co., Ltd.) thereto and perform stirring for 12 hours at room temperature.

Step (2): Perform centrifugation on the reacted mixture at 10,000 G for 60 minutes so as to remove the supernatant.

Step (3): Add ethanol so as to disperse the precipitates and perform centrifugation again. With the same procedure, perform washing with ethanol one time and with pure water one time.

The obtained nanoparticles modified with the amino group were subjected to FT-IR measurement. Adsorption due to the amino group was observed, and it was confirmed that the nanoparticles had been modified with the amino group.

Step (4): Adjust the nanoparticles modified with the amino group obtained at Step (3) to 3 nM by using PBS containing 2 mM of EDTA (ethylenediaminetetraacetic acid).

Step (5): Mix the solution adjusted at Step (4) with SM(PEG) 12 (Thermo Scientific, succinimidyl-[(N-maleomidopropionamid)-dodecaethyleneglycol]ester) so as to be a final concentration of 10 mM, and make it react for 1 hour.

Step (6): Perform centrifugation on the reacted mixture at 10,000 G for 60 minutes and remove the supernatant.

Step (7): Add PBS containing 2 mM of EDTA so as to disperse the precipitates and perform centrifugation again. With the same procedure, perform washing three times. Finally, perform re-dispersion by using 50 μL of PBS.

Step (8): Dissolve 100 μg of an anti Ki67 antibody in 100 μL of PBS, add 1M dithiothreitol (DTT) thereto, and make it react for 30 minutes.

Step (9): Remove excessive DTT from the reacted mixture with a gel filter column so as to obtain a reduced anti Ki67 antibody solution.

Step (10): Mix the particle dispersion obtained at Step (7) with the nanoparticles 1 as the starting material with the reduced anti Ki67 antibody solution obtained at Step (9) in PBS, and make it react for 1 hour.

Step (11): Add 4 μL of 10 mM mercaptoethanol so as to end the reaction.

Step (12): Perform centrifugation on the reacted mixture at 10,000 G for 60 minutes so as to remove the supernatant, and then add PBS containing 2 mM of EDTA so as to disperse the precipitates and perform centrifugation again. With the same procedure, perform washing three times. Finally, perform re-dispersion by using 500 μL of PBS, thereby obtaining the fluorescent substance-containing nanoparticles bonding with the anti Ki67 antibody.

The fluorescent substance-containing nanoparticles bonding with the anti Ki67 antibody obtained with the nanoparticles 1 as the starting material are defined as "staining reagent (a)".

(B) Staining of Tissue with Fluorescent Substance-Containing Nanoparticles

Immunostaining of human breast tissue sections was performed with the staining reagent (a) by the method of the following Steps (1) to (10). As the sections to stain, a tissue array slide (CB-A712) of Cosmo Bio, Co., Ltd. was used.

Step (1): Immerse each pathological section in a container containing xylene for 30 minutes. Change the xylene three times during the immersion.

Step (2): Immerse the pathological section in a container containing ethanol for 30 minutes. Change the ethanol three times during the immersion.

Step (3): Immerse the pathological section in a container containing water for 30 minutes. Change the water three times during the immersion.

Step (4): Immerse the pathological section in 10 mM citric acid buffer solution (pH 6.0) for 30 minutes.

Step (5): Perform autoclaving for 10 minutes at 121 degrees.

Step (6): Immerse the autoclaved section in a container containing PBS for 30 minutes.

Step (7): Put 1% BSA-containing PBS on the tissue and leave it as it is for 1 hour.

Step (8): Put the staining reagent (a) in which the anti Ki67 antibody is bonded, diluted with 1% BSA-containing PBS to 0.05 nM on the tissue section and leave it as it is for 3 hours.

Step (9): Immerse the stained section in a container containing PBS for 30 minutes.

Step (10): Perform hematoxylin staining after fixation with 4% neutral Paraformaldehyde solution for 10 minutes.

Step (11): Drip Aquatex, produced by Merck Chemicals, thereon and then place a cover glass thereon to seal.

For comparison, in Step (8) above, the tissue was reacted with an anti Ki67 monoclonal antibody used as a primary antibody and then with a secondary antibody labeled with gold colloidal particles of 0.8 nm used as a secondary antibody. Next, the diameter of the gold colloidal particle was enhanced with an agent for silver enhancement to visualize the gold colloid. The obtained sample was fixed with 1% Osmium tetraoxide for 1 hour at 4° C. and dehydrated with increasing ethanol concentration, followed by freeze-drying with t-butyl alcohol (JFD-300, JEOL, Tokyo), palladium deposition by ION SPUTTER E-1010 (Hitachi High-Technologies Corp.; Tokyo), and immuno-SEM observation using a scanning electron microscope S-3000N (by Hitachi, Ltd.).

(C) Image Analysis Processing

With respect to each of the tissue sections stained with the staining reagent (a), microscopic images (a bright field image and a fluorescence image) were acquired.

As a microscope, an upright microscope Axio Imager M2 produced by Carl Zeiss AG was used. The objective lens was set to 20 times. In obtaining a fluorescence image, each tissue section was irradiated with excitation light having a wavelength of 580 nm, an image of fluorescence having a wavelength of 610 nm emitted from the tissue section was formed, and a microscopic image (image data) was acquired with a camera (monochrome) set in the microscope.

The camera has 6.4 μm×6.4 μm as the pixel size, 1,040 pixels as the number of pixels in height and 1,388 pixels as the number of pixels in width (a capturing region of 8.9 mm×6.7 mm).

Figure 20:
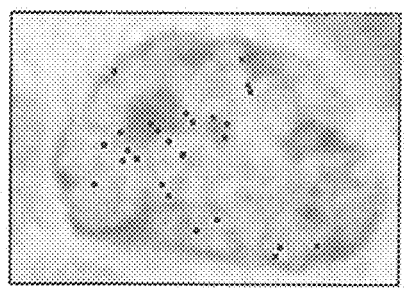
FIG. 20 is an image showing expression distribution of Ki67 protein according to Example 1.

The number and the location of nanoparticles 1 were calculated from the obtained images by the image analysis processing shown in FIG. 5, on the basis of luminance profiles. The distribution of Ki67 protein on a cell is shown in FIG. 20. The distribution corresponds to the location of expression according to the immuno-SEM observation using gold colloid. The information of the location of biological substance could be obtained easily.

Example 2

(A) Preparation of Staining Reagent (b)
(A-1) Preparation of Fluorescent Substance-Containing Nanoparticles (Nanoparticle 2; Green Melamine Particle)

Green melamine nanoparticles bonded with pyromethene dye (nanoparticles 2) were obtained as in the preparation of nanoparticles 1 in Example 1, except that 14.4 mg of pyromethene 556 (available from Exciton, Inc.), which is a green light emitting dye used as a fluorescent dye, was added to and dissolved in 22 ml of water.

The obtained nanoparticles 2 were observed under a scanning electron microscope and had an average particle size of 180 nm and a variation coefficient of 14%.

(A-2) [Bonding of Antibody to Fluorescent Substance-Containing Nanoparticles]

Fluorescent substance-containing nanoparticles bonding with the anti p53 antibody were obtained as in the bonding of antibody to the fluorescent substance-containing nanoparticles of Example 1, except that the nanoparticles 2 were used instead of nanoparticles 1 and anti p53 antibody were used instead of anti Ki67 antibody.

The fluorescent substance-containing nanoparticles bonding with the anti p53 antibody obtained with the nanoparticles 2 as the starting material are defined as "staining reagent (b)".

(B) Staining of Tissue with Fluorescent Substance-Containing Nanoparticles

Tissue staining was performed as in the Step (8) of the tissue staining with fluorescent substance-containing nanoparticles in Example 1, except that the staining reagent (a), which is bonding with the anti Ki67 antibody and diluted with 1% BSA-containing PBS to 0.05 nM, and the staining reagent (b), which is bonding with the anti p53 antibody and diluted with 1% BSA-containing PBS to 0.05 nM, was put on the tissue section and leave it as it is for 3 hours.

(C) Image Analysis Processing

With respect to each of the tissue sections stained with the staining reagent (a) and the staining reagent (b), microscopic images (a bright field image and fluorescence images) were acquired by the microscope described in Example 1.

Two fluorescence images were obtained, one by irradiating each tissue section with excitation light having a wavelength of 580 nm and forming an image of fluorescence having a wavelength of 610 nm to obtain and a fluorescence image data, and another by irradiating each tissue section with excitation light having a wavelength of 490 nm and forming an image of fluorescence having a wavelength of 520 nm to obtain and a fluorescence image data.

Figure 21:
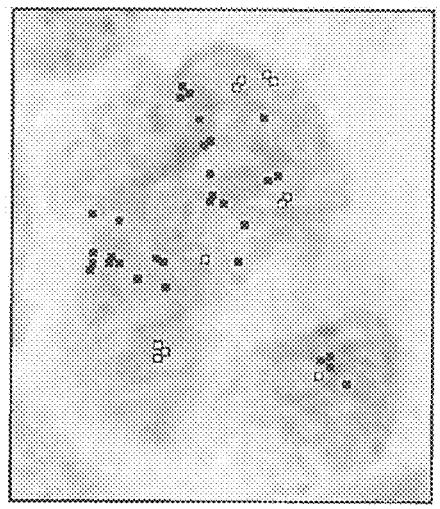
FIG. 21 is an image showing expression distribution of Ki67 protein and p53 protein according to Example 2.

The number and the location of the nanoparticles 1 and nanoparticles 2 were calculated from the obtained images by the image analysis processing shown in FIG. 5, on the basis of luminance profiles. As shown in FIG. 21, the distributions of two types of proteins, Ki67 protein and p53 protein, on cells could be displayed.

INDUSTRIAL APPLICABILITY

The present invention relates to an image processing technique for pathological diagnosis and can be suitably used, in particular, to easily and accurately quantitate expression of a specific protein in an observation target cell.

EXPLANATION OF REFERENCE NUMERALS

1A Microscopic Image Acquisition Device
2A Image Processing Device
3A Cable
21 Control Unit
22 Operation Unit
23 Display Unit
24 Communication I/F
25 Storage Unit
26 Bus
30 Cell Nucleus
40 Bright Point Region
42 Fluorescent Particle
50, 52 Bright Point Region
60, 62 Fluorescent Particle
100 Pathological Diagnosis Support System

The invention claimed is:
1. An image processing device comprising:
a memory storing a reference luminance profile of a single fluorescence particle; and
a processor including:
an input unit to input a bright field image showing a shape of a cell in a tissue section and a fluorescence image showing expression of a specific protein as a fluorescent bright point in the same range of the tissue section as the bright field image;
a first generation unit to generate a cell image showing an extracted specific site of the cell from the bright field image;
a second generation unit to generate an image showing an extracted bright point region from the fluorescence image, to generate a luminance profile for the bright point region, to identify extracted fluorescent particles in the extracted bright point region using the reference luminance profile, and to generate a fluorescent particle image showing the identified fluorescent particle in the bright point region; and an addition unit to add the cell image and the fluorescent particle image, thereby displaying the identified fluorescent particles in each cell of the cell image.

2. The image processing device according to claim 1, wherein the source of fluorescent bright point includes two or more types of fluorescent particles having different emission wavelengths from each other; and the second generation unit generates a fluorescent particle image for each type of the fluorescent particles.

3. A pathological diagnosis support system comprising:
the image processing device according to claim 1; and
an image acquisition device to acquire the bright field image and the fluorescence image used in the image processing device.

4. The image processing device according to claim 1, wherein the second generation unit determines how many fluorescent particles are present in the bright point region by comparing the reference luminance profile with the luminance profile for the bright point region.

5. An image processing method comprising;
an input step of inputting, to a processor, a bright field image showing a shape of a cell in a tissue section and a fluorescence image showing expression of a specific protein as a fluorescent bright point in the same range of the tissue section as the bright field image;

a first generation step of generating, by the processor, a cell image showing an extracted specific site of the cell from the bright field image;

a second generation step of generating, by the processor, an image showing an extracted bright point region from the fluorescence image, to generate a luminance profile for the bright point region, to identify extracted fluorescent particles in the extracted bright point region using a reference luminance profile of a single fluorescence particle, and to generate a fluorescent particle image showing the identified fluorescent particle in the bright point region; and an addition step of adding, by the processor, the cell image and the fluorescent particle image, thereby displaying the identified fluorescent particles in each cell of the cell image.

6. The image processing method of claim 5, wherein the second generation step includes determining how many fluorescent particles are present in the bright point region by comparing the reference luminance profile with the luminance profile for the bright point region.

* * * * *